United States Patent
Lai et al.

(10) Patent No.: US 7,140,875 B2
(45) Date of Patent: Nov. 28, 2006

(54) ORTHODONTIC BRACKET WITH REINFORCED TIEWINGS

(75) Inventors: Ming-Lai Lai, Arcadia, CA (US); Jirina V. Pospisil, Hacienda Heights, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 345 days.

(21) Appl. No.: 10/770,799

(22) Filed: Feb. 3, 2004

(65) Prior Publication Data
US 2005/0170308 A1 Aug. 4, 2005

(51) Int. Cl.
*A61C 3/00* (2006.01)

(52) U.S. Cl. .......................................................... 433/8
(58) Field of Classification Search ............. 433/8, 433/9, 10, 11, 12, 13, 14, 15, 16, 17, 18, 22, 433/24; D24/180
See application file for complete search history.

(56) References Cited

U.S. PATENT DOCUMENTS

| | | | |
|---|---|---|---|
| 2,368,851 A | 2/1945 | Laskin | |
| 3,578,744 A | 5/1971 | Wildman | |
| 3,765,091 A | 10/1973 | Northcutt | |
| 3,922,787 A * | 12/1975 | Fischer et al. | 433/15 |
| 3,964,165 A * | 6/1976 | Stahl | 433/8 |
| RE28,889 E | 7/1976 | Wildman | |
| 3,969,821 A | 7/1976 | Lee, Jr. et al. | |
| 4,107,844 A * | 8/1978 | Kurz | 433/9 |
| 4,216,583 A * | 8/1980 | Reynolds | 433/9 |
| 4,219,617 A * | 8/1980 | Wallshein | 433/8 |
| 4,531,911 A | 7/1985 | Creekmore | |
| 4,575,337 A * | 3/1986 | Fujita | 433/8 |
| D289,329 S | 4/1987 | Evans | |
| D290,040 S * | 5/1987 | Kelly | D24/180 |
| 4,669,980 A * | 6/1987 | Degnan | 433/8 |
| 4,820,151 A | 4/1989 | Pospisil | |
| 4,826,430 A * | 5/1989 | Chen et al. | 433/8 |
| D302,588 S * | 8/1989 | Jones | D24/180 |
| D303,708 S | 9/1989 | Pospisil | |
| 4,867,678 A * | 9/1989 | Parker | 433/8 |
| D304,077 S | 10/1989 | Pospisil | |
| 4,878,840 A | 11/1989 | Reynolds | |
| 4,936,773 A * | 6/1990 | Kawaguchi | 433/9 |
| D315,957 S | 4/1991 | Kelly et al. | |
| 5,030,089 A * | 7/1991 | Kawaguchi | 433/8 |
| D322,482 S | 12/1991 | Lanieri et al. | |
| 5,095,602 A | 3/1992 | Reher et al. | |
| D331,975 S | 12/1992 | Pospisil | |
| 5,254,002 A * | 10/1993 | Reher et al. | 433/8 |
| 5,269,681 A * | 12/1993 | Degnan | 433/11 |
| 5,358,402 A | 10/1994 | Reed et al. | |
| 5,366,372 A | 11/1994 | Hansen et al. | |

(Continued)

*Primary Examiner*—Eduardo C. Robert
*Assistant Examiner*—David Comstock
(74) *Attorney, Agent, or Firm*—James D. Christoff

(57) ABSTRACT

An orthodontic bracket has at least one tiewing and a groove behind the tiewing for receiving a ligature. The groove extends along a path that is inclined in a direction away from an archwire slot of the bracket as a central, upright reference plane bisecting the bracket is approached. In addition, the depth of the groove decreases as the reference plane is approached. Preferably, an outermost edge of at least one tiewing is inclined in a direction away from the archwire slot as the adjacent side of the bracket is approached. The tiewing is less likely to fracture during the course of orthodontic treatment, and yet the ease of ligation is not compromised.

25 Claims, 3 Drawing Sheets

U.S. PATENT DOCUMENTS

| | | |
|---|---|---|
| 5,380,196 A | 1/1995 | Kelly et al. |
| D358,649 S | 5/1995 | Moschik |
| 5,439,379 A * | 8/1995 | Hansen .......................... 433/8 |
| 5,441,408 A * | 8/1995 | Moschik ........................ 433/8 |
| 6,193,508 B1 * | 2/2001 | Georgakis .................... 433/11 |
| 6,648,638 B1 | 11/2003 | Castro et al. |
| 6,709,268 B1 | 3/2004 | Pospisil |
| 6,733,286 B1 * | 5/2004 | Abels et al. .................. 433/11 |
| 2003/0064342 A1 * | 4/2003 | Fukutomi ...................... 433/8 |
| 2003/0113683 A1 | 6/2003 | Puttler et al. |

* cited by examiner

ORTHODONTIC BRACKET WITH REINFORCED TIEWINGS

BACKGROUND OF THE INVENTION

1. Field of the Invention

This invention broadly relates to an appliance used in the course of orthodontic treatment to correct a malocclusion. More particularly, the present invention relates to an orthodontic bracket having at least one tiewing for ligating an archwire to the bracket.

2. Description of the Related Art

Orthodontic treatment involves movement of a patient's teeth to improved positions. Orthodontic treatment can improve the patient's occlusion, so that the teeth function better with each other during mastication. Orthodontic treatment can also greatly enhance a patient's facial appearance, especially in instances where the teeth adjacent the front of the oral cavity are noticeably crooked.

One type of orthodontic treatment system includes a set of tiny appliances known as brackets that are fixed to the patient's anterior, cuspid and bicuspid teeth. Each of the brackets has a slot to receive a resilient wire known as an archwire. The archwire functions as a track to guide movement of the brackets and hence movement of the associated teeth to desired positions. Ends of the archwire are often received in passages of small appliances known as buccal tubes that are fixed to the patient's molar teeth.

Orthodontic brackets often have small arms or wings known as tiewings that are adjacent the archwire slot. A groove extends behind each tiewing for receiving a ligature. In use, the practitioner extends the ligature behind one or more of the tiewings and also over the archwire in order to retain the archwire in the archwire slot. If the practitioner elects to replace the archwire during the course of treatment, the ligature is removed from its position behind the tiewings in order to release the archwire from the archwire slot.

In general, two types of orthodontic ligatures are in common use. One type of ligature resembles a tiny elastomeric O-ring, and is stretched during installation to fit behind the tiewings as well as over the archwire. When the elastomeric ligature is released, it contracts to hold the archwire in place. Another type of orthodontic ligature in common use is made of a segment of small-diameter metallic wire, and ends of the wire are twisted together to form a snug-fitting loop after the wire has been extended behind the selected tiewings and over the archwire.

Over the years, there has been increased interest in improving the aesthetics of orthodontic appliances so that the appliances are less noticeable during the course of treatment. Many attempts have been made to reduce the size of orthodontic appliances, and some ceramic appliances are as small as, for example, 3.5 mm in height and 3.0 mm in width. However, attempts to reduce the overall size of the bracket are often hampered at least in part by the tiewings, since the tiewings should extend outwardly a distance sufficient to reliably retain the ligature in place. If the ligature is accidentally dislodged from its position behind the tiewings, the archwire may release from the bracket with the result that the progress of treatment is interrupted.

In addition to reducing the overall size of orthodontic appliances, many manufacturers have introduced appliances made of a transparent or translucent material in order to render the appliance less noticeable and consequently more aesthetic in the oral cavity. Examples of suitable transparent and translucent materials include ceramic materials, such as monocrystalline and polycrystalline alumina. Appliances made of a plastic material such as polycarbonate are also available. Preferably, the transparent or translucent materials are colorless and transmit sufficient light to take on the color of the underlying tooth.

Appliances made of translucent and transparent ceramic materials are preferred by many practitioners. However, ceramic materials are relatively brittle and lack strength in tension. If the tiewings of ceramic brackets are too small, they may fracture when exposed to unexpectedly large forces during the course of treatment.

As can be appreciated, there is a continuing need in the art for an orthodontic bracket that is considered aesthetic by both the practitioner and the patient, and yet is constructed such that the probability of tiewing fracture is reduced.

SUMMARY OF THE INVENTION

The present invention is directed to an orthodontic bracket having one or more tiewings that are constructed to reduce the likelihood of tiewing fracture during treatment while securely retaining the ligature in place. The tiewings are reinforced by constructing the bracket in such a manner that the bracket material is gradually added along the ligature groove as the inner side of the tiewing or the center of the bracket is approached. This construction enables the overall size of the bracket to be significantly reduced, resulting in a bracket having an improved aesthetic appearance.

In more detail, the present invention is directed in one aspect toward an orthodontic bracket having a base, a body extending outwardly from the base and an archwire slot extending across the body. The bracket also has a mesial side and a distal side. The bracket also includes at least one tiewing next to the archwire slot and adjacent a certain one of the sides. The bracket also includes a groove behind the tiewing for receiving a ligature. The tiewing has an outermost edge, and at least a portion of the outermost edge is inclined in a facial reference plane in a direction away from the archwire slot as the certain side is approached. At least a portion of the groove extends in a direction that is inclined in a facial reference plane toward the archwire slot as the certain side is approached.

The present invention is also directed in another aspect toward an orthodontic bracket having a base, a body extending outwardly from the base and an archwire slot extending across the body. The bracket also has a mesial side and a distal side. The bracket also includes a mesial-occlusal tiewing and a mesial-gingival tiewing adjacent the mesial side, a distal-occlusal tiewing and a distal-gingival tiewings adjacent the distal side and a groove extending behind each tiewing for receiving a ligature. Each tiewing has an outermost edge and at least a portion of each outermost edge is inclined in a facial reference plane in a direction away from the archwire as the adjacent side of the bracket is approached. At least a portion of the groove extends in a direction that is inclined in a facial reference plane toward the archwire slot as the adjacent side of the bracket is approached.

Another aspect of the present invention is also directed toward an orthodontic bracket having a base, a body extending outwardly from the base and an archwire slot extending across the body. The bracket also has a mesial side and a distal side. The bracket also includes at least one tiewing next to the archwire slot and a groove behind the tiewing for receiving a ligature. The groove extends along a path from one of the sides of the bracket and in a direction generally toward a reference plane bisecting the bracket into mesial and distal halves. At least a portion of the groove decreases in depth in directions perpendicular to the path and toward the archwire slot as the reference plane is approached. At least a portion of the groove is inclined in a direction away from the archwire slot as the reference plane is approached.

An additional aspect of the present invention is also directed toward an orthodontic bracket having a base, a body extending outwardly from the base and an archwire slot extending across the body. The bracket also has a mesial side and a distal side. The bracket also includes a mesial-occlusal tiewing, a mesial-gingival tiewing, a distal-occlusal tiewing, a distal-gingival tiewing and a groove extending along a path behind each tiewing for receiving a ligature. At least a portion of the groove decreases in depth in directions perpendicular to the path and toward the archwire slot as a reference plane bisecting the bracket into mesial and distal halves is approached. At least a portion of the groove behind each tiewing is inclined in a direction away from the archwire slot as the reference plane is approached.

These and other aspects of the invention are described in more detail in the paragraphs that follow and are illustrated in the accompanying drawings.

DETAILED DESCRIPTION OF THE PREFERRED EMBODIMENTS

Figure 1:
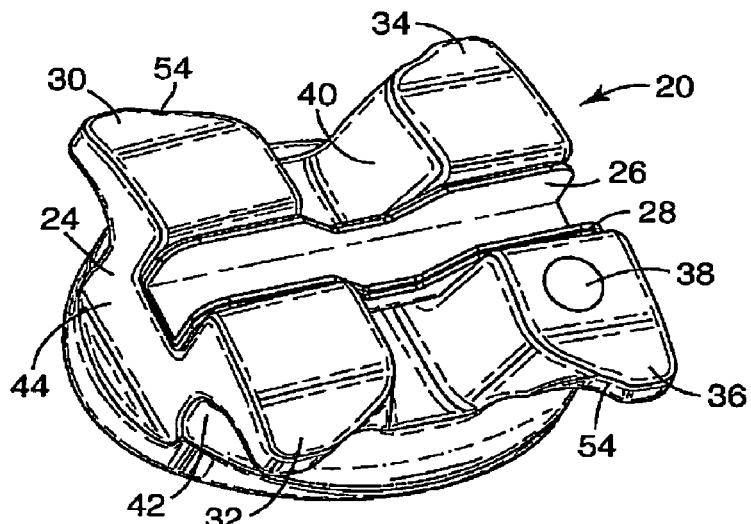
FIG. 1 is a perspective view of an orthodontic bracket constructed in accordance with one embodiment of the present invention, looking at the bracket toward its labial, gingival and mesial sides.

As used herein, "mesial" refers to a direction toward the middle of the patient's arch and "distal" refers to a direction away from the middle of the patient's arch. "Occlusal" refers to a direction toward the outer tips of the patient's teeth, while "gingival" refers to a direction toward the gums or gingiva. "Labial" refers to a direction toward the patient's lips or cheeks, while "lingual" refers to a direction toward the patient's tongue. A "facial plane" means a reference plane perpendicular to a reference axis extending in a labial-lingual direction.

An orthodontic bracket according to one embodiment of the invention is illustrated in FIGS. 1–7 and is broadly designated by the numeral 20. The bracket has a base 22 adapted for directly bonding to the enamel surface of a patient's tooth. Preferably, the base 22 has a compound concave contour that matches the compound convex contour of the patient's tooth surface.

Optionally, the base 22 is provided with a means for enhancing the strength of the bond between the bracket 20 and the patient's tooth. Bond enhancement means include chemical bond enhancements, mechanical enhancements or a combination of both. Examples of suitable chemical enhancements include silane treatment such as described in U.S. Pat. No. 4,948,366. Examples of mechanical bond enhancement include ridges, pegs, grooves, particles (such as regularly shaped particles including spheres, rods, and cones, and irregularly-shaped particles such as shards of ceramic material). Preferably, the mechanical bond enhancements include structure that provides undercut regions that serve to mechanically interlock the adhesive and the bracket 20 together once the adhesive has hardened.

The bracket 20 includes a body 24 that extends outwardly from the base 22 in a labial direction. An archwire slot 26 extends across the body 24 in a generally mesial-distal direction. In the embodiment shown in FIGS. 1–7, the archwire slot 26 is defined on three sides by an archwire slot liner 28.

The bracket 20 of this exemplary embodiment includes four tiewings, including a mesial-occlusal tiewing 30, a mesial-gingival tiewing 32, a distal-occlusal tiewing 34 and a distal-gingival tiewing 36. The distal-gingival tiewing 36 optionally includes a round index mark 38 that facilitates correct orientation of the bracket 20 on the patient's tooth. The archwire slot liner 28 extends through the space between the mesial tiewings 30, 32 as well as through the space between the distal tiewings 34, 36.

The bracket 20 also includes an upright channel 40 that optionally extends in a direction parallel or substantially parallel to an occlusal-gingival reference axis. The channel 40 extends along the space between the occlusal tiewings 30, 34, along the space between the gingival tiewings 32, 36 and behind the archwire slot liner 28 (i.e., lingually of the archwire slot liner 28). Preferably, the channel 40 has a depth in a lingual direction that is greater than the lingual depth of the archwire slot 26. As shown for example in FIG. 5. the channel 40 decreases in width in a mesial-distal direction as the base 22 is approached. Preferably, when the bracket 20 is mounted on the patient's tooth in its intended position, the channel 40 extends in a direction parallel to the long axis of the tooth and the archwire slot 26 extends in a direction parallel to the patient's occlusal plane.

The bracket 20 also includes a groove 42 that extends behind each of the tiewings 30–36 (i.e., is located in a lingual direction relative to the tiewings 30–36). The groove 42 is adapted to receive a ligature for ligating an archwire the archwire slot 26. In most instances, the practitioner will elect to extend the ligature behind all of the tiewings 30–36. However, in certain instances such as in instances where the tooth should be pivoted in a rotational direction about its long axis, the practitioner may elect to extend the ligature only behind the mesial tiewings 30, 32 or only behind the distal tiewings 34, 36.

The groove 42 extends along a curved path. One section of the curved path is adjacent an occlusal side of the body 24, and the other section of the curved path is adjacent the gingival side of the body 24. The curved path is shown in dashed lines in FIG. 6 behind the tiewings 32, 34, 36. The curved path is also shown in full line in areas of FIG. 6 where the mesial-occlusal tiewing 30 has been removed for purposes of illustration. The complete extent of the curved path is also shown in FIG. 7, which is a cross-sectional view taken along lines 7—7 of FIG. 5.

Each of the tiewings 30–36 extends outwardly from the archwire slot 26 a certain distance in directions parallel to an occlusal-gingival reference axis. Preferably, for each of the tiewings 30–36, this distance increases as the adjacent side of the bracket 20 is approached. More particularly, the distance of the extension of the mesial tiewings 30, 32 increases as a mesial side 44 of the bracket 20 is approached, and the distance of extension of the distal tiewings 34, 36 increases as a distal side 46 of the bracket 20 is approached. For exemplary purposes, a determination of this distance is presented by the extent of the vector labeled "A" in FIG. 6 for the distal-occlusal tiewing 34.

Each of the tiewings 30–36 has an outer section 48 and an inner section 50. The sections 48, 50 are equal in overall width in directions along the length of the archwire slot 26. Tn FIG. 6, the boundary between the outer section 48 and the inner section 50 is designated by the dashed line 52 for the tiewing 34. Preferably, for each of the tiewings 30–36, the overall, average length of the inner section of the tiewing is less than the overall, average length of the outer section of the tiewing, where such length is determined in a direction parallel to the long axis of the tooth. For example, and with reference to FIG. 6, the average length or distance as represented by the letter "A" of the inner section 50 is less than the overall, average length or distance of the outer section 48. This average distance or length is determined by calculating the average distance of an outermost occlusal edge 54 of the tiewing 34 away from the archwire slot 26 in directions parallel to the reference line "A" for both the outer section 48 as well as the inner section 50.

Figure 6:
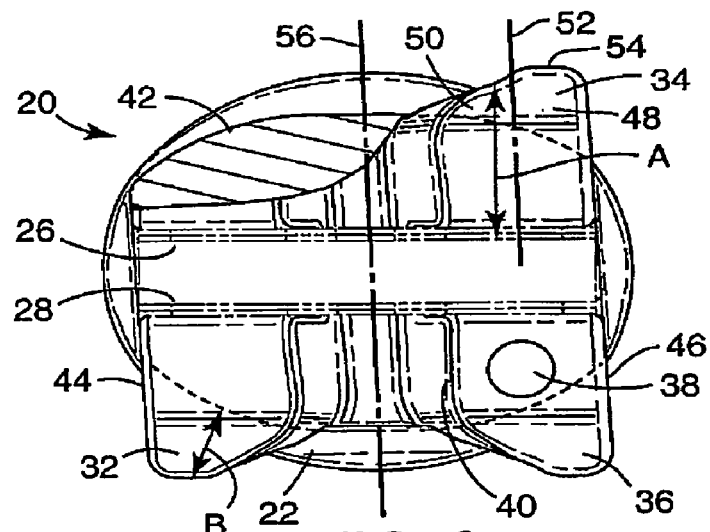
FIG. 6 is a view somewhat similar to FIG. 3 except that a portion of one of the tiewings of the bracket has been removed in order to better illustrate a groove for receiving a ligature.
Figure 7:
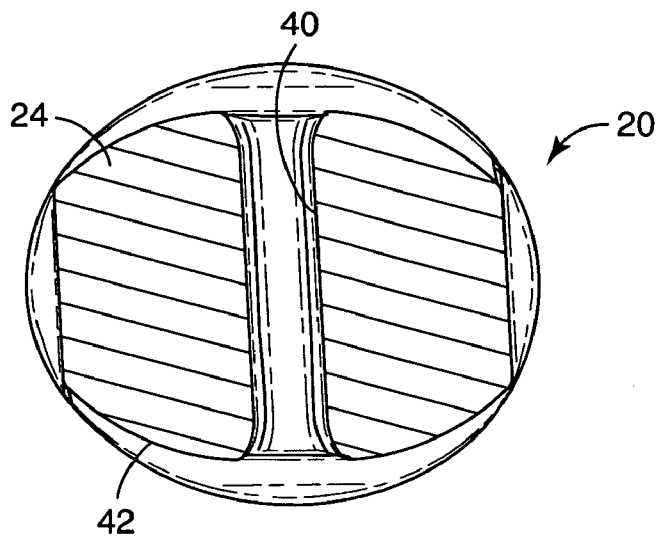
FIG. 7 is a cross-sectional view of the bracket shown in FIGS. 1–6 and taken along lines 7—7 of FIG. 5 illustrating the entire extent of the groove.

The edge of a reference plane 56 is also shown in FIG. 6. The reference plane 56 extends in an occlusal-gingival direction parallel to the direction of extension of the channel 40 or to the long axis of the tooth. The reference plane 56 bisects the bracket 20 into mesial and distal halves. As the groove 42 approaches the reference plane 56, the distance between the groove 42 and the archwire slot 26 increases in directions parallel to the reference plane 56. As the groove 42 approaches either the mesial side 44 or the distal side 46 of the bracket 20, the distance between the groove 42 and the archwire slot 26 decreases in directions parallel to the reference plane 56. The path of the groove 42 is inclined in a facial reference plane in a direction toward the archwire slot 26 as either of the sides 44, 46 is approached away from the reference plane 56. Similarly, the distance between the groove 42 and the archwire slot 26 increases in directions parallel to the reference plane 56 as the reference plane 56 is approached from either of the sides 44, 46.

For purposes herein, the "depth" of the groove 42 is determined at any point along the path of the groove 42 by determining the distance between the outermost edge 54 and the bottom of the groove 42 (i.e., nearest the mesial-distal and occlusal-gingival center of the bracket), wherein the distance is determined at that point along the groove 42 in a reference plane perpendicular to a line tangent to such point. For purposes of explanation, this distance is represented by the letter "B" in FIG. 6 at a point along the groove 42 that is adjacent the tiewing 32. As shown, the depth of the groove as represented by the letter "B" decreases as the reference plane 56 is approached.

When the bracket 20 is viewed in a lingual direction looking toward its labial side (i.e., in a direction perpendicular to a facial plane), the path of travel of the groove 42 converges with the direction of extension of the outermost edge 54 as the inner side of each tiewing 30–36 is approached. Conversely, the outermost edge 54 extends away from the path of travel of the groove 42 as the outer side of each tiewing 30–36 is approached. As shown for example in FIGS. 1, 3 and 6, the outermost edge 54 is inclined in a facial reference plane in a direction away from the archwire slot 26 as the certain side is approached for at least a majority of the width of the inner section 50. As a result, the depth of the groove 42 is greatest near the outer edge of the tiewing. Such construction facilitates ligation, since the groove 42 is deepest near the outermost corner of each tiewing and hooking the ligature behind the tiewing is facilitated.

The inclined path of the groove 42 as the reference plane 56 is approached in FIG. 6 has been found to provide an important advantage, in that such construction serves to reinforce the tiewings 30–36. As a result, the tiewings 30–36 are less likely to fracture when subjected to a crushing force (such as a force imposed on the tiewing in a lingual direction) or a torquing force (such as when the archwire tends to pivot about its long axis in the archwire slot 26 and impose a force on the tiewing in an occlusal or gingival direction). At the same time, the ease of ligating the bracket 20 to an archwire is not diminished because the outermost, distal-occlusal corner of each of the tiewings 30–36 extends a significant distance away from the bottom of the groove 42 to facilitate "catching" the ligature during ligation.

Figure 2:
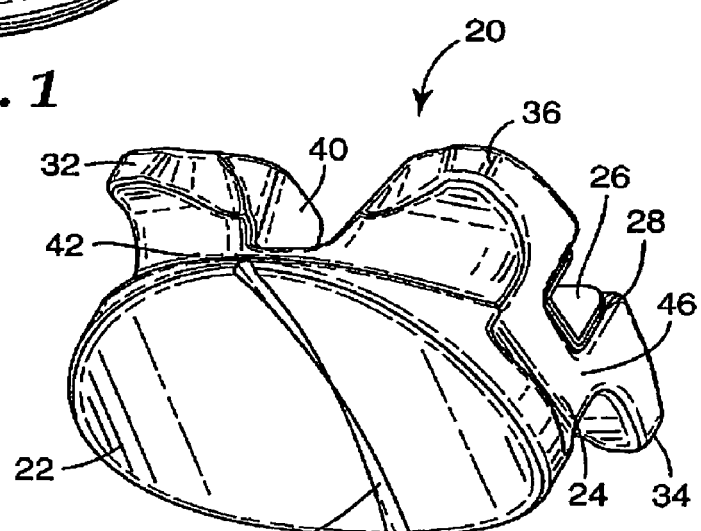
FIG. 2 is a perspective view of the bracket illustrated in FIG. 1, looking at the bracket toward its lingual, gingival and distal sides.
Figure 3:
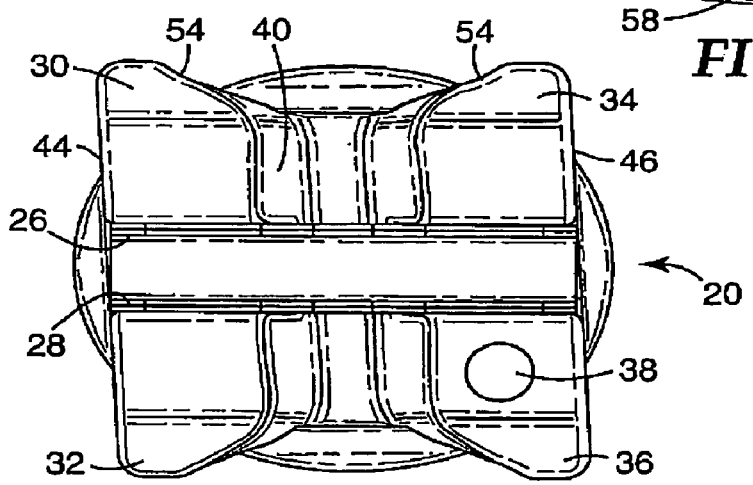
FIG. 3 is an elevational view of the bracket shown in FIGS. 1 and 2, looking at the bracket toward its labial side.
Figure 4:
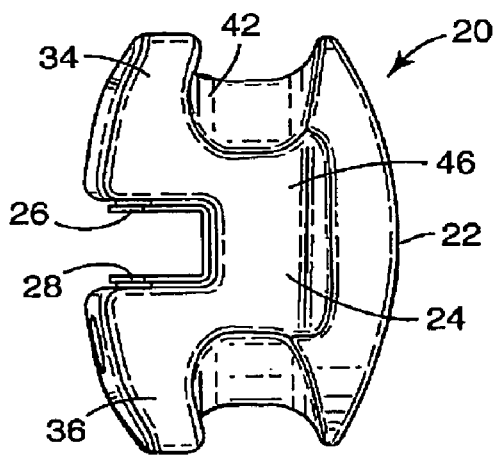
FIG. 4 is a side elevational view of the bracket shown in FIGS. 1–3, looking at the bracket in a direction toward its distal side.
Figure 5:
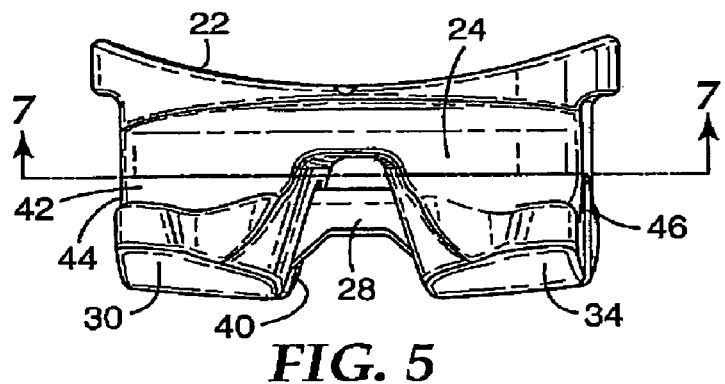
FIG. 5 is a top view of the bracket shown in FIGS. 1–4, looking at the bracket toward its occlusal side.

The bracket 20 also includes a second channel 58 that extends along the base 22 as shown in FIG. 2. The second channel 58 preferably extends parallel to and beneath the first channel 40. The channels 40, 58 facilitate removing the bracket 20 from the patient's tooth at the conclusion of treatment.

When the practitioner desires to debond the bracket 20, a pliers-type tool is placed over the body 24 such that one jaw of the tool engages the mesial side 44 of the bracket 20 and the other jaw of the tool engages the distal side 46 of the bracket 20. Next, the handles of the tool are squeezed together in order to urge the jaws against the mesial and distal sides 44, 46. As pressure is applied to the sides 44, 46, the body 24 fractures in a region between the lingual side of the first channel 40 and the labial side of the second channel 58, thereby enabling one or both of the mesial and distal halves of the bracket 20 to rock toward each other and detach from underlying areas of the tooth.

Additional aspects of the debonding procedure, along with further details and options for facilitating debonding are described in applicant's U.S. Pat. Nos. 5,366,372 and 5,439,379, both of which are expressly incorporated by reference herein.

Optionally, the archwire slot liner 28 is made of a metallic material that provides sliding mechanics similar to the sliding mechanics observed with brackets that are entirely made of a metallic material. Suitable materials for the archwire slot liner 28 include stainless steel, such as Series 300 or 17-4 PH stainless steel. Other materials may also be employed, such as titanium or gold, or materials having a stainless steel, titanium or gold coating. Additional examples of suitable materials (which may optionally be used as coating over another material) include alloys of cobalt and chromium, alloys of iron, nickel and chromium and combinations thereof.

Alternatively, the archwire slot liner 28 is made of a non-metallic material. Suitable non-metallic materials include, for example, plastic and zirconium.

The archwire slot liner 28 may be manufactured by any one of a number of techniques, and manufactured either separately from or together with the manufacture of the remaining components of the bracket 20. For example, the archwire slot liner 28 could be integrally made by a metal injection molding technique, by a machining process or by a casting process. Other techniques are described in applicant's U.S. Pat. Nos. 5,358,402 and 5,380,196, both of which are expressly incorporated by reference herein. The methods described in those references include methods where the liner is made in situ in the ceramic body.

In instances where the archwire slot liner 28 is manufactured separately from the body 24, any one of a number of methods may be subsequently used to couple the archwire slot liner 28 to the body 24. For instance, the archwire slot liner 28 may be connected to the body 24 by an adhesive, such as an epoxy or a dental or orthodontic adhesive. Other methods include a soldering process, a brazing process (such as the process described, for example, in the aforementioned U.S. Pat. Nos. 5,358,402 and 5,380,196) and a glazing technique (such as the use of a glass paste or a slurry that is heated to its softening or melting temperature).

The remaining components of the bracket 20 (i.e., the components other than the archwire slot liner 28) may be made of any one of a number of materials including plastic and ceramic materials. Suitable plastic materials include polycarbonate, which may optionally be reinforced with fibers. Suitable ceramic materials include monocrystalline as well as polycrystalline materials. Examples of monocrystalline materials include sapphire and single crystal aluminum oxide. Examples of polycrystalline materials include alumina-based ceramics such as described in U.S. Pat. Nos. 4,954,080 and 6,648,638, both of which are expressly incorporated by reference herein. If a ceramic material is employed, the ceramic may be injection molded or press molded to a desired shape, machined to a desired shape or constructed by a method that comprises a combination of molding and machining.

As another option, the bracket 20 may be made entirely of a ceramic material (including, for example, the ceramic materials described above), a plastic material (including, for example, the plastic materials described above) or a metallic material (such as stainless steel or titanium). In those instance, the facing sides of the tiewings may optionally serve as walls defining the archwire slot, and an archwire slot liner (such as liner 28) may be omitted.

Figure 8:
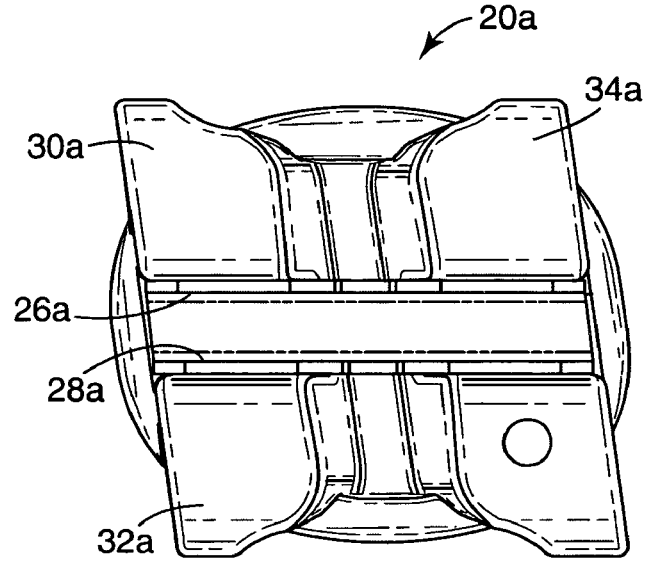
FIG. 8 is an elevational view of an orthodontic bracket constructed in accordance with another embodiment of the present invention, looking at the bracket toward its labial side.
Figure 9:
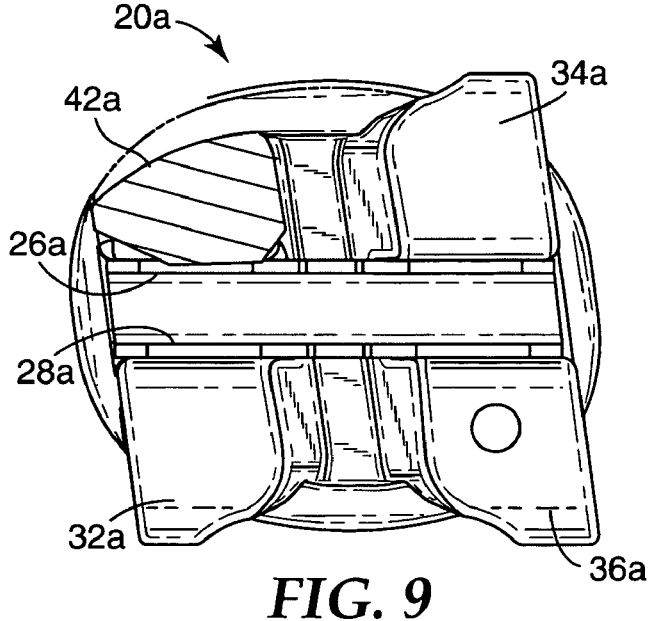
FIG. 9 is a view somewhat similar to FIG. 8 except that a portion of one of the tiewings of the bracket has been removed in order to better illustrate a groove for receiving a ligature.

An orthodontic bracket 20a according to another embodiment of the invention is illustrated in FIGS. 8 and 9. Except as described below, the bracket 20a is substantially identical to the bracket 20 and as a consequence a detailed description of the similar aspects need not be repeated.

The bracket 20a includes a mesial-occlusal tiewing 30a, and mesial-gingival tiewing 32a, a distal-occlusal tiewing 34a and a distal-gingival tiewing 36a. The tiewings 30a–36a are substantially similar to the tiewings 30–36, except that the tiewings 30a–36a are more angulated than the tiewings 30–36. For example, the mesial and distal sides of the tiewings 30a–36a, as well as a central axis of the tiewings 30a–36a, extend at a smaller angle relative to the central, longitudinal axis of the archwire slot 26a in comparison to the direction of extension of the mesial and distal sides of the tiewings 30–36 as well as the central axis of the tiewings 30–36 relative to the central, longitudinal axis of the archwire slot 26. In the exemplified embodiments, this angle is 82 degrees for the bracket 20a and is 87 degrees for the bracket 20.

FIGS. 8 and 9 also illustrate an archwire slot liner 28a that defines three sides of the archwire slot. FIG. 9 also depicts a ligature groove 42a that extends behind each of the tiewings 30a–36a.

Alternative constructions of the invention are possible. For example, the base (such as base 22) may have a shape that is generally square or rectangular when viewed in a lingual direction. As another example, the outermost edge of the tiewings (such as edge 54) may present when viewed in a lingual direction a shape that resembles a semicircle, a truncated "V", a non-symmetrical convex curve or a generally straight configuration that extends at an angle (relative to the archwire slot) from one side of the tiewing to the other.

A number of other options are also possible. For example, the bracket may only have one tiewing located on an occlusal or gingival side, and two tiewings located on the opposite side. As yet another option, the bracket may have a certain number of tiewings and only some of the tiewings are constructed in accordance with the embodiments described above. As still another option, the bracket may be a "self-ligating" bracket and include a latch or clip for connecting the archwire to the bracket. Examples of self-ligating brackets are shown, for example, in U.S. Pat. Nos. 6,582,226 and 6,302,688, both of which are expressly incorporated by reference herein.

Those skilled in the art will recognize that other variations are also possible. Accordingly, the invention should not be deemed limited to the particular embodiments that are set out in detail above, but instead only by a fair scope of the claims that follow along with their equivalents.

The invention claimed is:

1. An orthodontic bracket having a base, a body extending outwardly from the base and an archwire slot extending across the body, the bracket also having a mesial side and a distal side, the bracket also including at least one tiewing next to the archwire slot and adjacent a certain one of the sides, wherein the bracket also includes a groove behind the tiewing for receiving a ligature, wherein the tiewing has an outermost edge, wherein at least a portion of the outermost edge is inclined in a facial reference plane in a direction away from the archwire slot as the certain side is approached, wherein at least a portion of the groove extends in a direction that is inclined in a facial reference plane toward the archwire slot as the certain side is approached, wherein the tiewing has an outer section and an inner section that have equal widths in directions along the length of the archwire slot, and wherein the outermost edge is inclined in a facial reference plane in a direction away from the archwire slot as the certain side is approached for at least a majority of the width of the inner section.

2. An orthodontic bracket according to claim 1, wherein the outermost edge extends at an angle that lies approximately midway between a mesial-distal reference axis and an occlusal-gingival reference axis.

3. An orthodontic bracket according to claim 1 wherein the groove extends along a path, and wherein at least a portion of the path is curved.

4. An orthodontic bracket according to claim 3 wherein the path extends in a smooth curve along the entire extent of the tiewing.

5. An orthodontic bracket according to claim 1 wherein the groove has a depth that is determined in directions perpendicular to the path of the groove and toward the archwire slot, and wherein the depth of the groove decreases as a reference plane bisecting the bracket into mesial and distal halves is approached.

6. An orthodontic bracket according to claim 1 wherein the bracket comprises a ceramic material.

7. An orthodontic bracket having a base, a body extending outwardly from the base and an archwire slot extending across the body, the bracket also having a mesial side and a distal side, the bracket also including a mesial-occlusal tiewing and a mesial-gingival tiewing adjacent the mesial side, a distal-occlusal tiewing and a distal-gingival tiewing adjacent the distal side and a groove extending behind each tiewing for receiving a ligature, wherein each tiewing has an outermost edge, wherein at least a portion of each outermost edge is inclined in a direction away from the archwire slot as the adjacent side of the bracket is approached, wherein at least a portion of the groove extends in a direction that is inclined toward the archwire slot as the side adjacent each tiewing is approached, wherein the body also includes a channel extending between at least two of the tiewings in a direction substantially parallel to an occlusal-gingival reference axis, and wherein the channel decreases in width in a mesial-distal direction as the base is approached.

8. An orthodontic bracket according to claim 7 wherein at least a portion of each outermost edge extends in a direction at an angle oriented approximately midway between a mesial-distal reference axis and an occlusal-gingival reference axis.

9. An orthodontic bracket according to claim 8 wherein the groove extends along a certain path, and wherein the path crosses the outermost edge when viewed in a lingual direction.

10. An orthodontic bracket according to claim 7 wherein the bracket comprises a ceramic material.

11. An orthodontic bracket according to claim 7 wherein at least a portion of the groove extends along a path that is curved.

12. An orthodontic bracket according to claim 11 wherein the path extends in a smooth curve along the entire extent of each tiewing.

13. An orthodontic bracket having a base, a body extending outwardly from the base and an archwire slot extending across the body, the bracket also having a mesial side and a distal side, the bracket also including at least one tiewing next to the archwire slot and a groove behind the tiewing for receiving a ligature, wherein the tiewing has an outermost edge, wherein the groove extends along a path from one of the sides of the bracket and in a direction generally toward a reference plane bisecting the bracket into mesial and distal halves, wherein at least a portion of the groove decreases in depth in directions perpendicular to path and toward the archwire slot as the reference plane is approached, wherein at least a portion of the groove is inclined in a direction away from the archwire slot as the reference plane is approached, wherein the tiewing has an outer section and an inner section that have equal widths in directions along the length of the archwire slot, and wherein the outermost edge is inclined in a facial reference plane in a direction away from the archwire slot as the certain side is approached for at least a majority of the width of the inner section.

14. An orthodontic bracket according to claim 13 wherein at least a portion of the path is curved.

15. An orthodontic bracket according to claim 14 wherein the path extends in a smooth curve along the entire extent of the tiewing.

16. An orthodontic bracket according to claim 13 wherein the bracket comprises a ceramic material.

17. An orthodontic bracket according to claim 13 wherein the tiewing has an outermost edge, and wherein at least a portion of the outermost edge extends at an angle located between a mesial-distal reference axis and an occlusal-gingival reference axis.

18. An orthodontic bracket according to claim 13 wherein the bracket has at least one mesial tiewing and at least one distal tiewing, and wherein the groove extends along the path behind each of the tiewings, and wherein the groove decreases in depth in directions perpendicular to the path and toward the archwire slot as the reference plane is approached from either tiewing.

19. An orthodontic bracket having a base, a body extending outwardly from the base and an archwire slot extending across the body, the bracket also having a mesial side and a distal side, the bracket also including a mesial-occlusal tiewing, a mesial-gingival tiewing, a distal-occlusal tiewing, a distal-gingival tiewing and a groove extending along a path behind each tiewing for receiving a ligature, wherein at least a portion of the groove decreases in depth in directions perpendicular to the path and toward the archwire slot as a reference plane bisecting the bracket into mesial and distal halves is approached, wherein at least a portion of the groove behind each tiewing is inclined in a direction away from the archwire slot as the reference plane is approached, wherein the body also includes a channel extending between at least two of the tiewings in a direction substantially parallel to an occlusal-gingival reference axis, and wherein the channel decreases in width in a mesial-distal direction as the base is approached.

20. An orthodontic bracket according to claim 19 wherein at least a portion of the path is curved.

21. An orthodontic bracket according to claim 20 wherein the path extends in a smooth curve along the entire extent of each tiewing.

22. An orthodontic bracket according to claim 19 wherein the bracket comprises a ceramic material.

23. An orthodontic bracket according to claim 19 wherein each tiewing has an outermost edge, and wherein at least a portion of each outermost edge extends at an angle located between a mesial-distal reference axis and an occlusal-gingival reference axis.

24. An orthodontic bracket according to claim 23 wherein the path crosses each outermost edge when the bracket is viewed in a lingual direction.

25. An orthodontic bracket according to claim 19 wherein the groove decreases in depth in directions perpendicular to the path and toward the archwire slot as the reference plane is approached from either tiewing.

* * * * *

UNITED STATES PATENT AND TRADEMARK OFFICE
CERTIFICATE OF CORRECTION

PATENT NO. : 7,140,875 B2  Page 1 of 1
APPLICATION NO. : 10/770799
DATED : November 28, 2006
INVENTOR(S) : Ming-Lai Lai It is certified that error appears in the above-identified patent and that said Letters Patent is hereby corrected as shown below:

Column 5
Line 21, Delete "Tn" and insert -- In --, therefor.
Line 32, Delete "outennost" and insert -- outermost --, therefor.

Column 9
Line 42, In Claim 13, delete "hewing" and insert -- tiewing --, therefor.

Signed and Sealed this

Thirteenth Day of February, 2007

JON W. DUDAS
*Director of the United States Patent and Trademark Office*